United States Patent
Björn et al.

(10) Patent No.: US 6,848,908 B2
(45) Date of Patent: Feb. 1, 2005

(54) ARRANGEMENT COMPRISING A SPACER ELEMENT FOR AN IMPLANT, SUCH A SPACER ELEMENT AND A SCREWDRIVER FOR FASTENING THE SPACER ELEMENT

(75) Inventors: Göran Björn, Onsala (SE); Lars Jörneus, Frillesås (SE)

(73) Assignee: Nobel Biocare AB, Göteborg (SE)

( * ) Notice: Subject to any disclaimer, the term of this patent is extended or adjusted under 35 U.S.C. 154(b) by 0 days.

(21) Appl. No.: 10/239,057

(22) PCT Filed: Mar. 22, 2001

(86) PCT No.: PCT/SE01/00627

§ 371 (c)(1),
(2), (4) Date: Jan. 7, 2003

(87) PCT Pub. No.: WO01/70127

PCT Pub. Date: Sep. 27, 2001

(65) Prior Publication Data

US 2003/0162149 A1 Aug. 28, 2003

(30) Foreign Application Priority Data

Mar. 23, 2000 (SE) ................................................ 0001022

(51) Int. Cl.[7] ................................................ A61C 8/00
(52) U.S. Cl. ...................................... 433/173; 433/172
(58) Field of Search ................................ 433/173, 174, 433/175, 176, 172, 141; 81/460, 461

(56) References Cited

U.S. PATENT DOCUMENTS

| | | | | |
|---|---|---|---|---|
| 3,213,719 A | * | 10/1965 | Kloack | |
| 5,069,622 A | * | 12/1991 | Rangert et al. | 433/173 |
| 5,251,521 A | * | 10/1993 | Burda et al. | 81/460 |
| 5,370,021 A | * | 12/1994 | Shigematsu | 81/436 |
| 5,408,905 A | * | 4/1995 | Mikic et al. | 81/460 |
| 5,577,912 A | * | 11/1996 | Prins | 433/172 |
| 5,662,474 A | * | 9/1997 | Jorneus et al. | 433/172 |
| 5,947,733 A | * | 9/1999 | Sutter et al. | 433/173 |

FOREIGN PATENT DOCUMENTS

WO 9521589 8/1995

* cited by examiner

*Primary Examiner*—Cary E. O'Connor
(74) *Attorney, Agent, or Firm*—Venable LLP; Eric J. Franklin

(57) ABSTRACT

An arrangement including a spacer element operative to support a superstructure and including a first passage and a second passage. The second passage is operative to permit mechanical anchoring of the holder. A first screw is operative to screw the spacer element into an implant. During an initial stage of insertion the first passage is operative to receive the first screw such that a center axis of the first screw is inclined in relation to a direction of screwing of the first screw. During a final stage of insertion the first passage permits the first screw to tilt such that the center axis of the first screw substantially coincides with the direction of screwing. A holder is operative to hold the spacer element. The holder substantially prevents the first screw from leaving the position it has assumed during the final stage of insertion. A second screw is operative to screw the superstructure onto the spacer element.

20 Claims, 5 Drawing Sheets

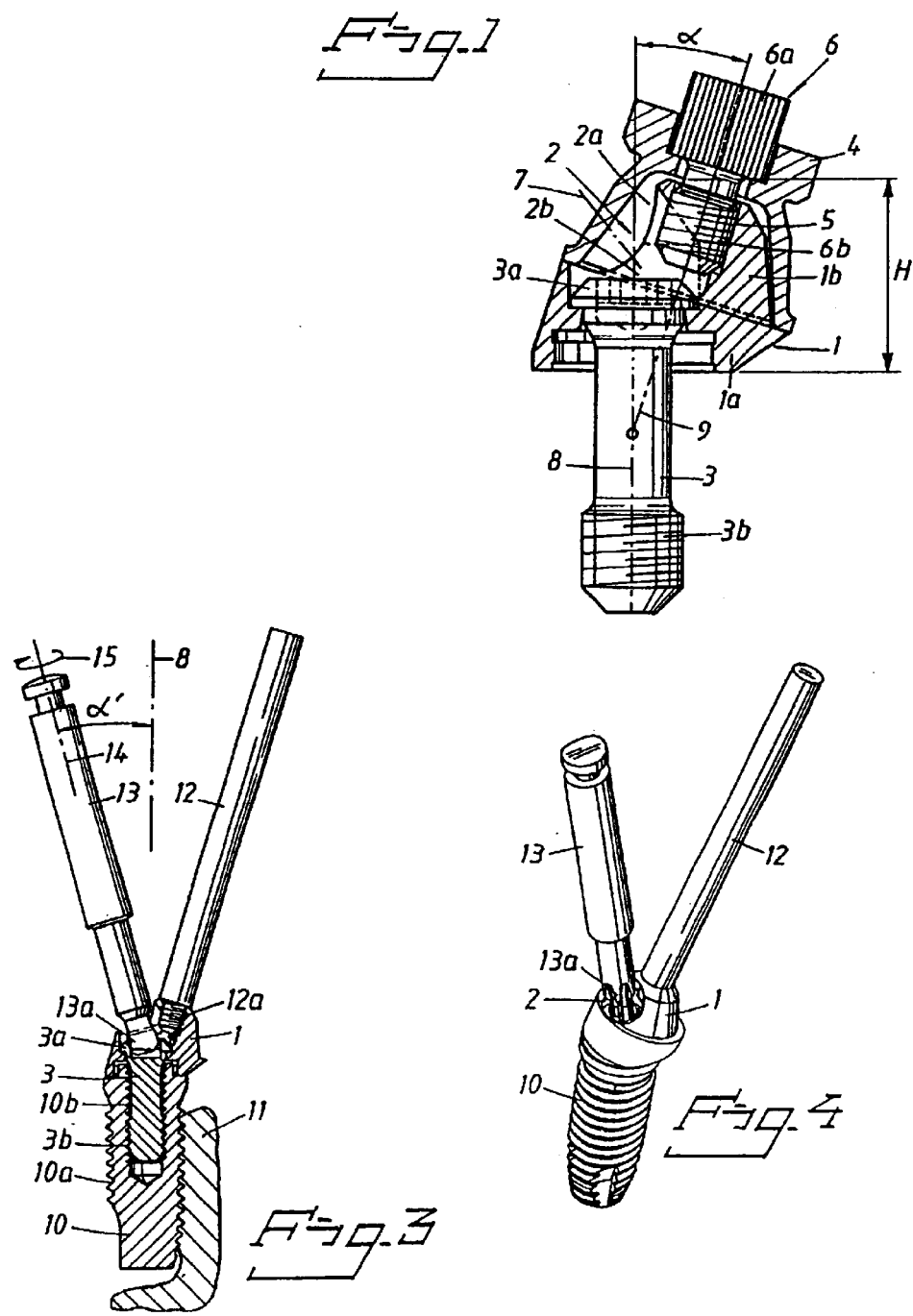

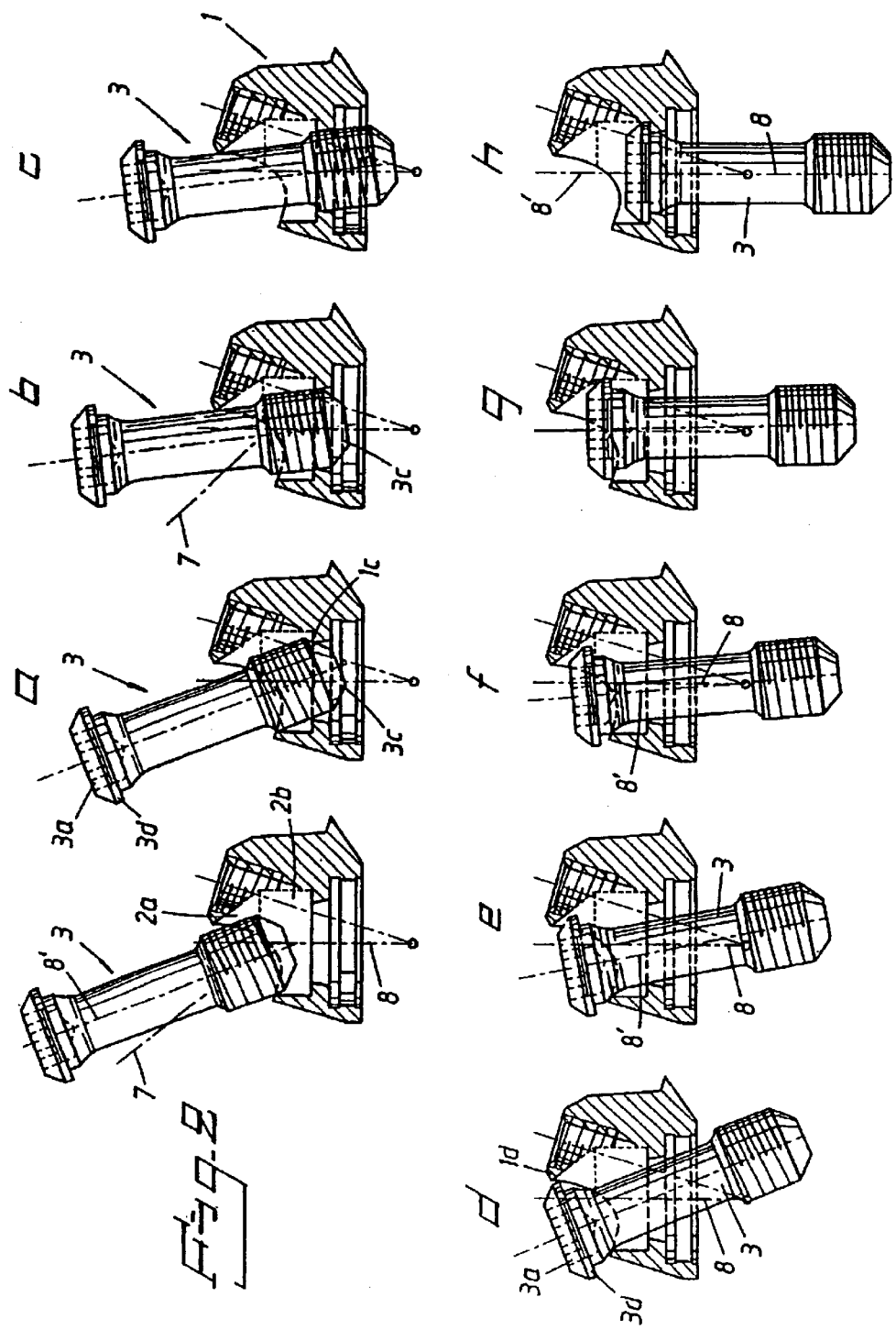

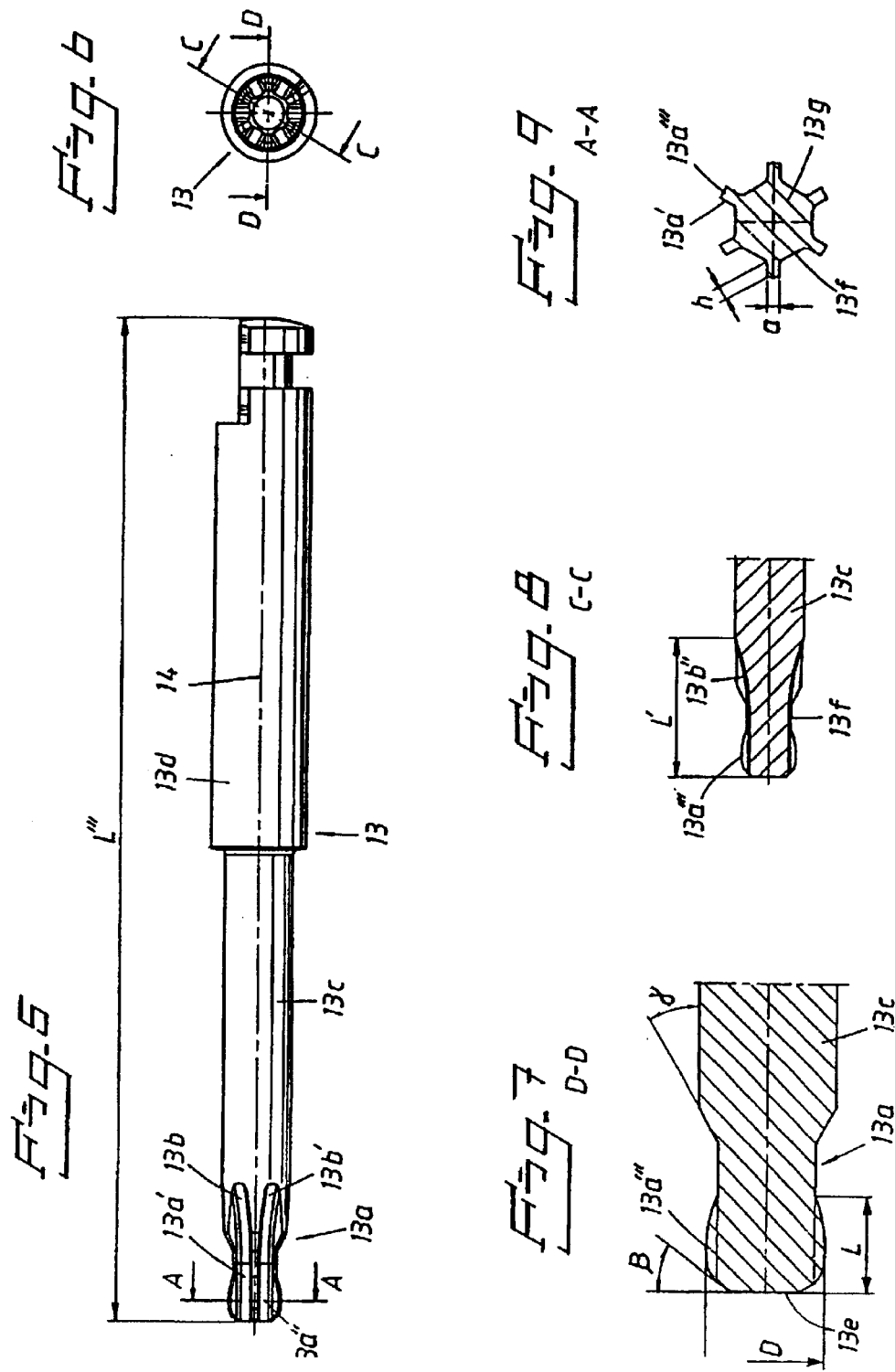

Figure 13A:
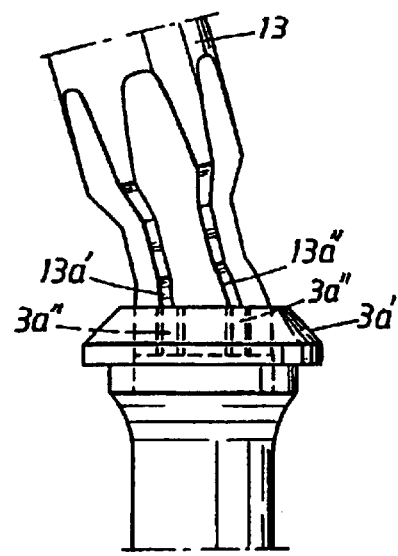

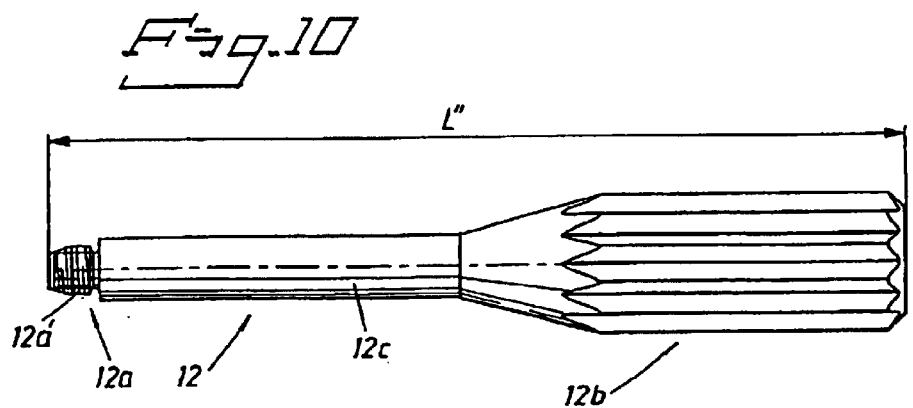

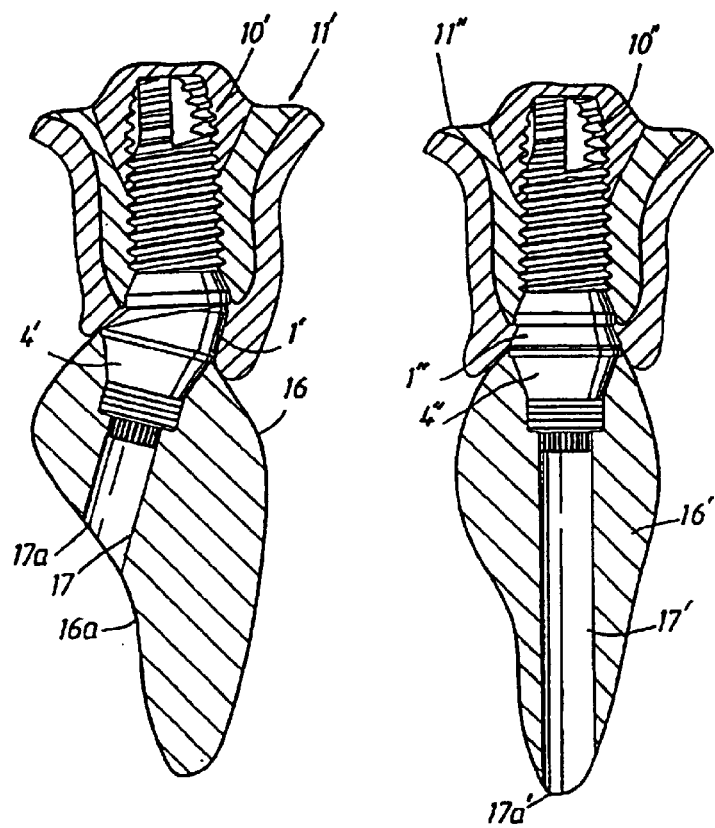

ARRANGEMENT COMPRISING A SPACER ELEMENT FOR AN IMPLANT, SUCH A SPACER ELEMENT AND A SCREWDRIVER FOR FASTENING THE SPACER ELEMENT

The present invention relates to an arrangement comprising a spacer element which can be fastened in an implant with a first screw which can be acted on by means of a screwdriver which can be introduced into the head of the first screw via a first passage arranged in the spacer element, for screwing it into a first thread in the implant. The spacer element will be designed to support a superstructure, for example in the form of a crown, bridge part, etc., which can be fastened to the spacer element with a second screw which can be acted on by means of said screwdriver, or a second screwdriver which can be introduced into the head of the second screw via a second passage arranged in the superstructure, for screwing the second screw into a second thread in the spacer element. The invention also relates to a spacer element for an implant, preferably a dental implant, which can be screwed securely in the implant by means of a first screw which is applied via a first passage and is designed to support a superstructure of said type. The superstructure in turn can be screwed securely in the spacer element by means of a second screw which is applied via a second passage which is inclined in relation to a direction of screwing of the first screw. The invention also relates to an arrangement which comprises a spacer element, preferably an angled spacer element for the implant, a holder for the spacer element, and a screwdriver. The spacer element can be screwed securely in the implant by means of a first screw which is assigned a first passage in the spacer element. The spacer element is intended to support said superstructure and for this purpose has a second passage for a second screw, by means of which the superstructure can be secured in the spacer element. The invention also relates to a screwdriver for screwing in the implant and/or the spacer element for the implant and/or the superstructure on said spacer element, implant, etc.

The invention is a development of the spacer element for tooth implants according to Swedish Patent 9400448-8 (502433). The known spacer element comprises a base portion for connection to a fixture implanted in the jaw bone, and an upper part with a substantially conical limit surface for connection to a tooth prosthesis. The base portion comprises a through-hole for a spacer screw which is intended to engage with an internally threaded bore in the upper portion of the fixture and thereby form a first screw connection for locking the spacer element in a defined direction of deflection in relation to the fixture. The upper part comprises a second screw connection for connection of the tooth prosthesis, which screw connection forms a fixed angle in relation to the first screw connection. In the present application, the term fixture is equivalent to implant, and the connection functions for the spacer element to the implant and tooth prosthesis or superstructure can in principle constitute the same basic elements.

In the dental field, there is a need to be able to extend the range and improve the various functions obtained with the range in question. The known angled spacer element is characterized, for example, by a quite considerable structural height and the upper connection portion has a fairly small cone angle, which limits the direction of insertion of the tooth prosthesis or equivalent which can have several supports which are not mutually parallel. There is therefore a need to be able to produce spacer elements with a lower structural height and despite this be able to increase the cone angle so that there is more space for the actual superstructure and greater freedom as regards the choice of cone angle for the purpose of increasing the directions of insertion of respective tooth prostheses. It is an object of the invention to solve the above problems, among others.

There is also a need to be able to simplify the assembly or insertion function in situ (in the patient), which means that components must be able to be fitted in advance in a simple and straightforward manner. The components in question are in terms of volume relatively very small and difficult to handle. The invention aims to solve this problem too.

As regards the use of a screwdriver in connection with small screws, it is difficult to access them with the screwdriver, among other reasons because the screws and the screwdrivers now used presuppose that a purely axial direction of fitting is employed. If the axial direction of fitting can be omitted, great advantages can be achieved from the assembly point of view. The invention also solves this problem.

In dental contexts it is often desirable to be able to tighten the screws in question by setting an angle between the directions of application and tightening of the screwdriver and screw, respectively. Thus, for example, reference can be made to the above case of angled spacer elements. Reference may also be made to cases where, when attaching a dental bridge or a superstructure to the spacer element or implant, it is often desirable to design the dental bridge or superstructure with an angled screw channel (passage) so that the mouth of the channel can be on an aesthetically unimportant surface, for example on the inside or occlusal surface of the dental bridge. The invention aims to solve this problem too.

That which can principally be regarded as characterizing an arrangement according to the invention is that the first passage and/or the second passage are arranged with a centre line, or each with their respective centre line, in the longitudinal direction of the respective passage, which is set at an angle in relation to the direction of screwing of the respective screw and thus the respective screwdriver is set at an angle relative to said direction or directions of screwing when the screwdriver is applied via its front parts into the respective screw head and the respective screw is tightened in its associated thread.

Further developments of this arrangement are set out below.

That which can principally be regarded as characterizing a spacer element according to the invention is that the first passage has a first passage part whose centre axis in the longitudinal direction is inclined in relation to the direction of screwing of the first screw and to the centre axis of the second passage in the longitudinal direction. Further characteristics are that the first passage has a second passage part whose centre axis in the longitudinal direction substantially coincides with the direction of screwing of the first screw, and-that the first passage is designed to receive the front parts of the first screw in a direction in which the centre axis of the first screw substantially coincides with the centre axis of the first passage part during an initial stage of insertion, and, in a final stage of insertion, to permit a tilting movement of the first screw or a transverse movement of the upper parts of the first screw. After said tilting or transverse movement, the first screw assumes a position in the second passage part in which its centre axis substantially coincides with the centre axis of the second passage.

In one illustrative embodiment of the inventive concept, the first passage is arranged to permit a temporary tilting movement of the first screw in an intermediate stage of insertion, in order to allow its front parts to pass a flange or surface cooperating with the screw head. Further embodiments of the spacer element according to the invention are set out in attached subclaims 8 to 11.

An arrangement according to the invention can be regarded as being characterized by the fact that, during an initial stage of insertion, the first passage is designed to receive the front parts of the first screw, with the centre axis of the first screw inclined in relation to the direction of screwing of the first screw. Further characteristics are that the first passage is designed, during a final stage of insertion, to permit tilting movements of the first screw and thus cause the centre axis of the first screw to substantially coincide with the direction of screwing. In addition, the spacer element, preferably by means of said second passage, is designed to permit mechanical anchoring of the holder mentioned earlier. The latter is designed to prevent the first screw from leaving the position it has assumed in said final stage, i.e. to prevent the first screw from dropping out of the spacer element. The holder and the spacer element anchored therein and the first screw applied in the last-mentioned position can thereafter be applied to the implant at the same time as the screwdriver mentioned earlier can cooperate via its front parts with the screw head in order to tighten the first screw in a thread in the implant, with the front parts of the screwdriver set at an angle in relation to the direction of screwing of the first screw.

In one embodiment of the arrangement, the holder has a front threaded part via which the holder can be screwed into a corresponding inner thread for the second screw in the spacer element, resulting in a single easily maneuverable unit with holder and spacer element.

That which can principally be regarded as characterizing a screwdriver according to the invention is that the front parts of the screwdriver engage in grooves on the respective screw head even if a centre axis of said front parts, upon application of these in said grooves, and upon rotational transmission of the front parts to the screw, diverges from the direction of screwing of the screw.

Further developments of the screwdriver according to the invention are set out below.

The features proposed above considerably facilitate the handling of components of small volume. By inserting the spacer screw or the first screw in position through a partially laterally directed opening on the spacer element, the upper attachment part of the spacer element can be designed with a much lower height than was previously possible. Another very important advantage is that the height of the attachment part makes it possible to obtain a much greater cone angle than was previously possible within the given maximum diameter of the upper portion of the spacer element. It therefore becomes possible to design these upper portions with greater divergence than was previously possible, while at the same time it is still possible to apply the superstructure or dental bridge. The fact that the spacer element is provided with a holder which, for example, can be screwed securely in the threaded hole simplifies the fitting of the spacer element. This holder is also designed such that it prevents the screw head from moving out of the spacer element. It is now possible, for example, to make available spacer elements with different cone angles, for example cone angles of 0, 17, 30°.

Figure 13B:
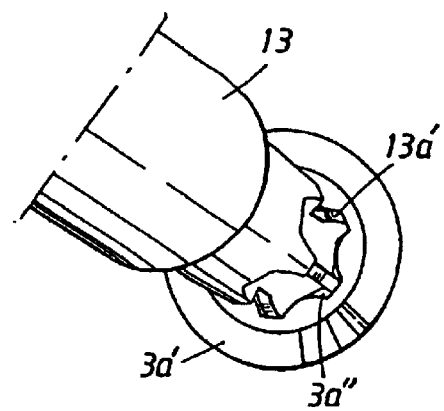
Figure 14:
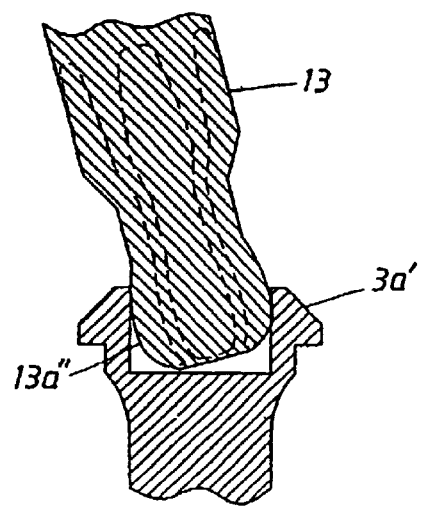

A presently proposed embodiment of an arrangement, a spacer element and a screwdriver according to the invention will be described below with reference to the attached drawings, in which:

FIG. 1 is a vertical section showing an angled spacer element in which a first fastening screw assumes a final position and in which a superstructure has been screwed securely into the spacer element with a second screw, FIGS. 2 to 2h are vertical sections showing a sequence for application of the first screw in an angled spacer element according to the invention, FIG. 3 is a vertical section showing a spacer element with a holder secured thereon, and with a first screw screwed into an implant by means of a screwdriver, FIG. 4 shows a perspective view, obliquely from above, of the arrangement according to FIG. 3, FIG. 5 shows a lengthways view of a screwdriver according to the invention, FIG. 6 shows an end view of the screwdriver according to FIG. 5, FIG. 7 is a longitudinal section showing parts of the screwdriver according to FIG. 5 and viewed along a section D—D in FIG. 6, FIG. 8 is a longitudinal section showing parts of the screwdriver according to FIG. 5 and viewed along a section C—C in FIG. 6, FIG. 9 is a cross section of an embodiment of the front parts of the screwdriver, viewed along a section A—A in FIG. 5, FIG. 10 shows a side view of the holder according to FIGS. 3 and 4, FIG. 11 is a longitudinal section showing an angled spacer element applied to an implant in a jaw or tooth bone, and to which spacer a superstructure has been applied, with a connection channel extending through the inside of the artificial tooth, FIG. 12 is a vertical section showing the application of a non-angled spacer element to an implant in a tooth bone, where the connection channel for the second screw extends at an angle to the spacer element, FIG. 13 shows, from the side (a) and from above (b), examples of a screw head with a groove arrangement which can be used in this context, and FIG. 14 is a vertical section showing the front parts of the screwdriver cooperating with grooves on a screw head.

In FIG. 1, an angled spacer element is indicated by 1. The angled spacer element has a base part 1a and a cone-shaped part 1b. The spacer element is also provided with a first passage 2 which comprises a first passage part 2a and a second passage part 2b. Via the first passage or the passage parts 2a and 2b the spacer element has received a first screw 3 which has a head 3a and a thread 3b at its free end. A superstructure 4 has been applied in a known manner to the cone-shaped part 1b and this superstructure 4 is screwed into the spacer element via a second passage 5 by means of a second screw 6 which is provided in a known manner with a head 6a and a thread 6b arranged at its front end, by means of which the superstructure 4 is screwed with the screw 6 into the spacer element 1b in a corresponding thread in the passage 5. The first passage part 2a of the first passage has a centre axis 7 which is set at an angle in relation to the direction of screwing 8 of the screw 3 which substantially coincides with the centre axis of the first screw. The second passage part 2b thus has a centre axis which substantially coincides with the direction of screwing or axis 8 shown in FIG. 1. The second screw 6 and the recess 5 in the spacer element, into which the second screw can be screwed, are assigned a centre axis 9 which is set at an angle in relation to the direction of screwing 8. An angle a between the axes 8 and 9 symbolizes a deflection angle which the implant is designed for. In the present case, the angle a shown in FIG. 1 is ca. 17°. The spacer element can be designed for angles between 15 and 45°, and, thus, angled spacer elements with 17 and 30° can be made available on the market. The spacer element 1 has a low height H, which means values in the range of 6 to 12 mm, for example ca. 10 mm.

FIG. 2 shows the initial stage of an insertion or receiving procedure for the first screw 3 in the first passage which, in accordance with the above, consists of the first and second passage parts 2a and 2b. It will be seen here that the centre axis 8' of the implant is inclined in relation to the direction of screwing 8. The first screw can thus be applied at an angle into said first passage or recess and substantially adjoin the centre axis 7 of the first passage part 2a.

In accordance with FIG. 2a, insertion in this direction can be continued until the front parts 3c of the first screw abut a contact flange for a bottom surface 3d on the head 3a of the first screw.

FIG. 2b shows that in a subsequent intermediate stage of the insertion or receiving procedure for the first screw 3, the latter can be tilted temporarily such that the angle in relation to the centre axis 7 of the first passage part becomes greater, which means that said front parts 3c are free of the flange 1c and that the lowering or insertion procedure can continue.

In accordance with FIG. 2c, the first screw 3 has been inserted further into the spacer element 1. The continued insertion has taken place in substantially the same direction as in the case according to FIG. 2b.

In the position according to FIG. 2d, the final stage of the insertion procedure is approached. In this position, the lower surface 3d of the screw head 3a must be free of the edge 1d of the spacer element, which means that the screw 3 must once again be inclined more strongly in relation to the direction of insertion 8 or more closely adjoin the centre axis 7 of the first passage part.

In the final stage according to FIG. 2e, the first screw assumes a position in which the first screw can be tilted or its head can be displaced sideways so that its centre axis 8' can begin to approach the direction of screwing 8.

In FIG. 2f, the tilting movement has begun and the connection between the centre line 8 and the centre axis 8' begins to approach, i.e. the angle between the centre line and the centre axis is smaller than in FIG. 2e.

In FIGS. 2g and 2h, the final stage has definitively started and ended, respectively. According to FIG. 2h, the centre axis 8' now assumes a position which substantially coincides with the future screwing direction for the first screw 3.

In FIG. 3, the first screw 3 has been screwed into an implant 10 which can be an implant of a type known per se and which has been applied in a manner known per se in a partially illustrated jaw bone 11 via its outer thread 10a or outer threads. Before the implant 10 is screwed in, the spacer element 1 has been provided with a holder 12 whose front part 12a has been applied in the screw hole of the second screw (cf. 5 above). Said part 12a is designed with an outer thread which can cooperate with the inner thread by means of which the second screw 6 can be screwed into the spacer element. The spacer element 1 and the holder 12 thus form a common unit which is easy to handle and apply to the dental situation in question, i.e. to the implant 10 which is assumed to have become incorporated in the tooth bone or jaw bone 11. The part 12a of the holder 12 has an extent in the recess (cf. 4 in FIG. 1) for the second screw which means that the first screw cannot drop out of the position it has assumed according to FIG. 2h above. This means that spacer element and holder with inserted screw 3 according to FIG. 2h can be handled with great freedom when screwing in the implant. Thus, for example, the holder and spacer element can be turned upside down in relation to the position according to FIG. 3, without the first screw 3 leaving its recess. Spacer element, holder and screw 3 can thus be applied to the implant with the front parts of the screw 3 in the inner thread 10b of the implant, into which thread the screw 3 is to be screwed. In the initial stage of insertion, the screwdriver 13 is applied with its front parts 13a against the screw head, which on its upper face is designed in a manner known per se with one or more grooves. The longitudinal axis of the screwdriver 13 is indicated by 14 and, upon introduction of the screwdriver into the first passage (cf. 2 according to the above), the screwdriver can assume an angle α' in relation to the direction of screwing 8. Said front parts 13a of the screwdriver are thus arranged so that the front parts can penetrate into the groove on the top face of the screw head 3a. In accordance with what will be described below, said front parts are also arranged to permit the screwing of the first screw by rotational movements 15 of the screwdriver, despite the fact that said inclination α' is maintained. The angle α' can assume values of 10 to 45° and is preferably ca. 15 to 20°.

FIG. 4 shows how the holder 12 and the screwdriver 13 are inclined in relation to each other and in relation to the direction of screwing shown in FIG. 3. In addition, this figure shows the first passage 2 which is arranged in the spacer element 1 and via which the front parts 13a of the screwdriver can engage so that, despite the inclination, it is possible to screw the first screw into its thread in the implant 10. FIG. 4 also shows the design of said front parts.

FIGS. 5 and 6 show the screwdriver 13. Arranged at the front parts 13a there are projecting first wing-shaped elements 13a', 13a'' and also rear projecting wing-shaped elements 13b, 13b'. The front parts are supported by a part 13c which merges into a thicker grip part 13d. The parts 13a, 13c and 13d are arranged around a common centre axis 14.

According to FIG. 7, the first wing-shaped elements are provided with concave formations (as seen from the body) which can have a length L in the range of 1.0 to 1.3 mm. The diameter D across the outer edges 13a''' can assume values of 1.3 to 1.6 mm. Said concave outer edges 13a''' on the first wing-shaped elements extend rearwards from the end face 13e of the front parts at an angle α of ca. 30°. The termination of said front parts 13a towards the part 13c is effected via a bevel which is formed with an angle of ca. 30°.

FIG. 8 shows how the front concave wing-shaped elements 13a'' terminated on a body surface 13f, and that behind this body surface 13f there are second wing-shaped elements 13b'' which merge at the rear into said part 13c. A total length L' of the first and second wing-shaped elements and the intermediate body surface 13f can be chosen at ca. 2.5×L or in the range of 1.6 to 2.0 mm.

According to FIG. 9, the wing-shaped elements 13a''' are evenly distributed about the body 13g. Said wing-shaped elements have a height h, above the baby or its surface 13f, of 1.0 to 1.4 mm. The width or thickness a of the elements is adapted to the grooves on the first and second screws and can be between 0.1 and 0.2 mm. The wing-shaped elements are uniformly distributed about the body surface and are thus arranged at ca. 60° in the case shown in FIG. 9, where six wing-shaped elements have been used.

FIG. 10 shows the holder 12 according to FIG. 3 in more detail. The holder has a grip part, and its front parts 12a are provided with an outer thread 12a'. The grip part 12b merges into a narrower intermediate part 12c which at its end bears said front parts 12a. The holder 12 has substantially the same length L" as the screwdriver according to FIG. 5, in which figure the screwdriver length has been shown as L'''. Said lengths can be ca. 25 mm. At its front parts, the holder can have a diameter of 1.5 to 2.0 mm, for example.

FIG. 11 shows an example of the use of the spacer element in a dental situation where an implant 10' is implanted in a tooth bone or jaw bone 11'. The spacer element 1' is an angled spacer element which supports a superstructure 4' in accordance with the above. The superstructure has an artificial tooth 16. In accordance with the invention, a connection channel 17 for screwing the superstructure in the spacer element can be chosen such that a suitable exit point 17a is obtained on the superstructure, for example on the inside 16a of the artificial tooth.

FIG. 12 shows an alternative dental situation in which a straight spacer element 1" has been screwed into the implant 10" in a bone 11", for example a tooth bone or jaw bone. The superstructure 4" is therefore not angled in this case and, despite this, the connection channel 17' can extend through the artificial tooth 16' in such a way that its mouth 17a' comes to lie at a suitable point on the artificial tooth. It will thus be appreciated that there is great freedom of choice as regards the extents of the channels 17, 17'.

As regards the groove structure in the first and second screw heads, reference may be made to generally known groove arrangements or geometric configurations. In FIG. 13, a screw head 3a' has been shown in two views a and b, with an associated typical groove 3a" for cooperation with the screwdriver 13. In accordance with the above, the wing-shaped elements 13a', 13a" and their curved or concave end edges 13a''' on the screwdriver are adapted to the width of the groove 3a" in question so that each respective element securely penetrates into the groove. The width of the grooves exceeds the width a (see FIG. 9) of the wing-shaped elements 13a', 13a" etc. engaged in the groove 3a". As regards the materials of the various components, conventional components can be used, see the abovementioned Swedish patent on which the present invention is based. The screws, spacer element, holder and screwdriver can be made of conventional materials, and thus the spacer elements and implants can be made of titanium, the screws of gold or alloy, and the holder and screwdriver of steel or alloy. Alternatively, a second screwdriver, for example a screwdriver with another concave extent of the outer edge of the respective element, or a straight screwdriver, can be used for screwing the screw in at the angle 0.

FIG. 14 is a longitudinal section showing the cooperation between the screwdriver 13 and the screw head 3a' where a wing-shaped element has engaged in the corresponding groove 3a" so that parts of the concave end edge 13a'" bear against the bottom surface of the groove.

The invention is not limited to the embodiment shown above by way of example and instead can be modified within the scope of the attached patent claims and the inventive concept.

What is claimed is:

1. An arrangement, comprising:
a spacer element operative to support a superstructure, the spacer comprising a first passage having an opening and a center line and a second passage having an opening and a center line along a longitudinal axis, at least one of the center lines being arranged at an angle with respect to a direction of screwing, the first passage being operative to receive a first screw operative to be fastened in an implant and operative to receive a screwdriver to act on the first screw, the first passage being arranged at an angle relative to a direction of screwing of the first screw, the second passage being operative to receive a second screw and a screwdriver operative to act on the second screw, the second screw being operative to fasten the superstructure to the spacer;
wherein the center lines angled with respect to the direction of screwing set the screwdrivers at an angle relative to the directions of screwing when the screwdriver is applied via its front parts into the respective screw head and the respective screw is tightened in its associated thread.

2. The arrangement according to claim 1, wherein the superstructure comprises a crown or bridge part.

3. The arrangement according to claim 1, wherein the spacer element comprises an angled spacer element in which the center lines of the first passage and the second passage are angled with respect to each other.

4. The arrangement according to claim 1, wherein the first passage comprises a first passage part having a center line angled with respect to the direction of screwing, and a second passage part comprising having a center line substantially coinciding with the direction of screwing.

5. The arrangement according to claim 1, wherein the first passage is operative to receive the first screw at an angle that substantially coincides with the center line of the first passage part, and operative to allow the first screw in a position of insertion near the end position of the screw in the spacer element to tilt such that the first screw assumes a position in which the longitudinal axis of the first screw substantially coincides with the center line of the second passage part.

6. The arrangement according to claim 1, wherein at least one of the longitudinal extent and longitudinal direction of the second passage is arranged in the superstructure in relation to the direction of screwing of the second screw can be chosen as a function of the predetermined extent of the passage in an outer surface on the superstructure.

7. The arrangement according to claim 6, wherein the outer surface on the superstructure comprises an outer surface on the inside or outside of a tooth replacement.

8. A spacer element for a dental implant, comprising:
a first passage operative to receive a first screw, the first passage comprising a first passage part having a longitudinal axis inclined with respect to a direction of screwing of the first screw, the first passage further comprising a second passage part having a longitudinal axis substantially coinciding with the direction of screwing of the first screw, the first passage being operative to receive front parts of the first screw in a direction such that during an initial stage of insertion a center line of the first screw substantially coincides with the center line of the first passage part and to permit a tiling movement of the first screw during a final stage of insertion, wherein after the tilting movement the first screw assumes a position in the second passage part such that a longitudinal axis of the first screw substantially coincides with the center line of the second passage; and
a second passage inclined with respect to the direction of screwing of the first screw and with respect to the longitudinal axis of the first passage, the second passage being operative to receive a second screw, wherein the second screw is operative to screw a superstructure onto the spacer element.

9. The spacer element according to claim 8, wherein the first passage permits in an intermediate stage of insertion a temporary tilting movement of the first screw in order to allow its front part to pass a flange or surface which can cooperate with the head of the screw.

10. The spacer element according to claim 8, wherein the screwdriver comprises an angled spacer element having a height of 6 to 12 mm.

11. The spacer element according to claim 8, wherein the screwdriver comprises an angled spacer element having a height of 10 mm.

12. The spacer element according to claim 8, wherein an angle between the center axis of the passage part/the direction of screwing of the first screw and the center axis of the second passage is 15° to 45°.

13. The spacer element according to claim 8, wherein an angle between the center axis of the passage part/the direction of screwing of the first screw and the center axis of the second passage is 0°, 17° or 30°.

14. The spacer element according to claim 8, wherein the first passage is operative to receive front parts of a screwdriver for interaction with a head of the first screw, and thereby providing the front parts an angle which corresponds to an angle between the longitudinal axis of the first passage part and the direction of screwing, and wherein the first passage part is operative to support the front parts during the insertion of the first screw.

15. An arrangement, comprising:
   a spacer element operative to support a superstructure and comprising a first passage and a second passage, wherein the second passage is operative to permit mechanical anchoring of the holder,
   a first screw operative to screw the spacer element into an implant, wherein during an initial stage of insertion the first passage is operative to receive the first screw such that a center axis of the first screw is inclined in relation to a direction of screwing of the first screw and during a final stage of insertion the first passage permits the first screw to tilt such that the center axis of the first screw substantially coincides with the direction of screwing; and
   a holder operative to hold the spacer element, wherein the holder substantially prevents the first screw from leaving the position it has assumed during the final stage of insertion; and
   a second screw operative to screw the superstructure onto the spacer element.

16. The arrangement according to claim 15, wherein the spacer element is an angled spacer element.

17. The arrangement according to claim 15, wherein the superstructure comprises a crown or bridge part.

18. The arrangement according to claim 15, wherein the holder comprises a front threaded part operative to be screwed into the second passage to mechanically anchor together the holder and the spacer element, thereby forming a maneuvering unit with holder and spacer element.

19. An arrangement, comprising:
   a spacer element operative to support a superstructure and comprising a first passage and a second passage, wherein the second passage is operative to permit mechanical anchoring of the holder;
   a first screw operative to screw the spacer element into an implant, wherein during an initial stage of insertion the first passage is operative to receive the first screw such that a center axis of the first screw is inclined in relation to a direction of screwing of the first screw and during a final stage of insertion the first passage permits the first screw to tilt such that the center axis of the first screw substantially coincides with the direction of screwing, and wherein the first passage permits the first screw to be tightened into a thread of the implant by a screwdriver with its head set at an angle in relation to a direction of screwing of the first screw; and
   a holder operative to hold the spacer element, wherein the holder substantially prevents the first screw from leaving the position it has assumed during the final stage of insertion; and
   a second screw operative to screw the superstructure onto the spacer element.

20. The arrangement according to claim 19, wherein the holder comprises a front threaded part operative to be screwed into the second passage to mechanically anchor together the holder and the spacer element, thereby forming a maneuvering unit with holder and spacer element.

* * * * *